US00PP33894P2

(12) United States Plant Patent
Randag

(10) Patent No.: US PP33,894 P2
(45) Date of Patent: Jan. 18, 2022

(54) CALLA LILY PLANT NAMED 'DOZANWHIHO'

(50) Latin Name: *Zantedeschia sprengeri*
Varietal Denomination: Dozanwhiho

(71) Applicant: Dümmen Group B.V., De Lier (NL)

(72) Inventor: Cecilius Jan-Jochem Randag, Koedijk (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/313,079

(22) Filed: May 6, 2021

(51) Int. Cl.
*A01H 5/02* (2018.01)
*A01H 6/10* (2018.01)

(52) U.S. Cl.
USPC ..... Plt./490

(58) Field of Classification Search
USPC ..... Plt./263.1, 490
See application file for complete search history.

*Primary Examiner* — Susan McCormick Ewoldt
*Assistant Examiner* — Karen M Redden
(74) *Attorney, Agent, or Firm* — The Webb Law Firm

(57) ABSTRACT

'Dozanwhiho' is a new variety of calla lily plant having white colored spathes with a purple/pink throat spot that produces 6-10 inflorescences per 16-18 cm tuber. The flower stems are about 30-40 cm in height. The leaves are brownish green to dark green with maculations present and a smooth texture.

2 Drawing Sheets

Botanical classification: *Zantedeschia sprengeri*.
Varietal denomination: 'Dozanwhiho'.

BACKGROUND OF THE NEW PLANT

The present invention comprises a new and distinct variety of calla lily, botanically known as *Zantedeschia sprengeri* and hereinafter referred to by the varietal name 'Dozanwhiho'. 'Dozanwhiho' is a product of a planned breeding program, which had the objective of creating *Zantedeschia* hybrids for pot flower production in a wide range of colors with a classic flower shape. The new cultivar is a seedling selected from the crossing of *Zantedeschia sprengeri* variety 'Fangio' (female parent, U.S. Plant Pat. No. 28,196) with *Zantedeschia sprengeri* seedling Z050867-9107 (male parent, unpatented). 'Dozanwhiho' was selected in 2014 by the inventor in 't Zand, The Netherlands as one flowering plant within the progeny of the stated cross.

The first act of asexual reproduction of 'Dozanwhiho' by tissue culture was performed by the inventor in November of 2014 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants at approximately 11 weeks from planting in 14 cm pots in 't Zand, The Netherlands under greenhouse conditions, which approximate those generally used in horticultural practice. Color references are made to The 2001 R.H.S. Colour Chart of The Royal Horticultural Society of London, $4^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Dozanwhiho' which, in combination, distinguish this calla lily as a new and distinct cultivar:

1. Medium white colored spathes with a purple/pink colored throat spot;
2. Dark to brownish green colored leaves; and
3. Medium leaf maculations present.

The new variety is similar to its female parent in the following traits: throat spot presence, strong flower curve, lanceolate leaf shape, and the presence of leaf maculations. However, 'Dozanwhiho' exhibits a broader spathe width and longer spathe and spadix length than its female parent. Further, 'Fangio' has pink colored spathes, yellow/red spadix color, and red/green stem color. The new variety is similar to its male parent in the following traits: strong flower curve, long spadix length, green stem color, and the presence of leaf maculations. However, 'Dozanwhiho' exhibits a lighter spathe color, narrower spathe width, and shorter spathe length than its male parent. Further, its male parent does not exhibit a spathe throat spot and has a purple spadix color.

When compared to calla lily plant named 'Diva Siberia' (U.S. Plant Pat. No. 32,492), both varieties exhibit white colored spathes, but 'Diva Siberia' is a variety of *Zantedeschia aethiopica* and does not exhibit a spathe throat spot or leaf maculations.

BRIEF DESCRIPTION OF THE DRAWINGS

The accompanying photographic drawings illustrate the new variety taken at approximately 11 weeks of age, with the colors being as nearly true as is possible with color illustrations of this type.

DESCRIPTION OF THE NEW PLANT

Figure 1:
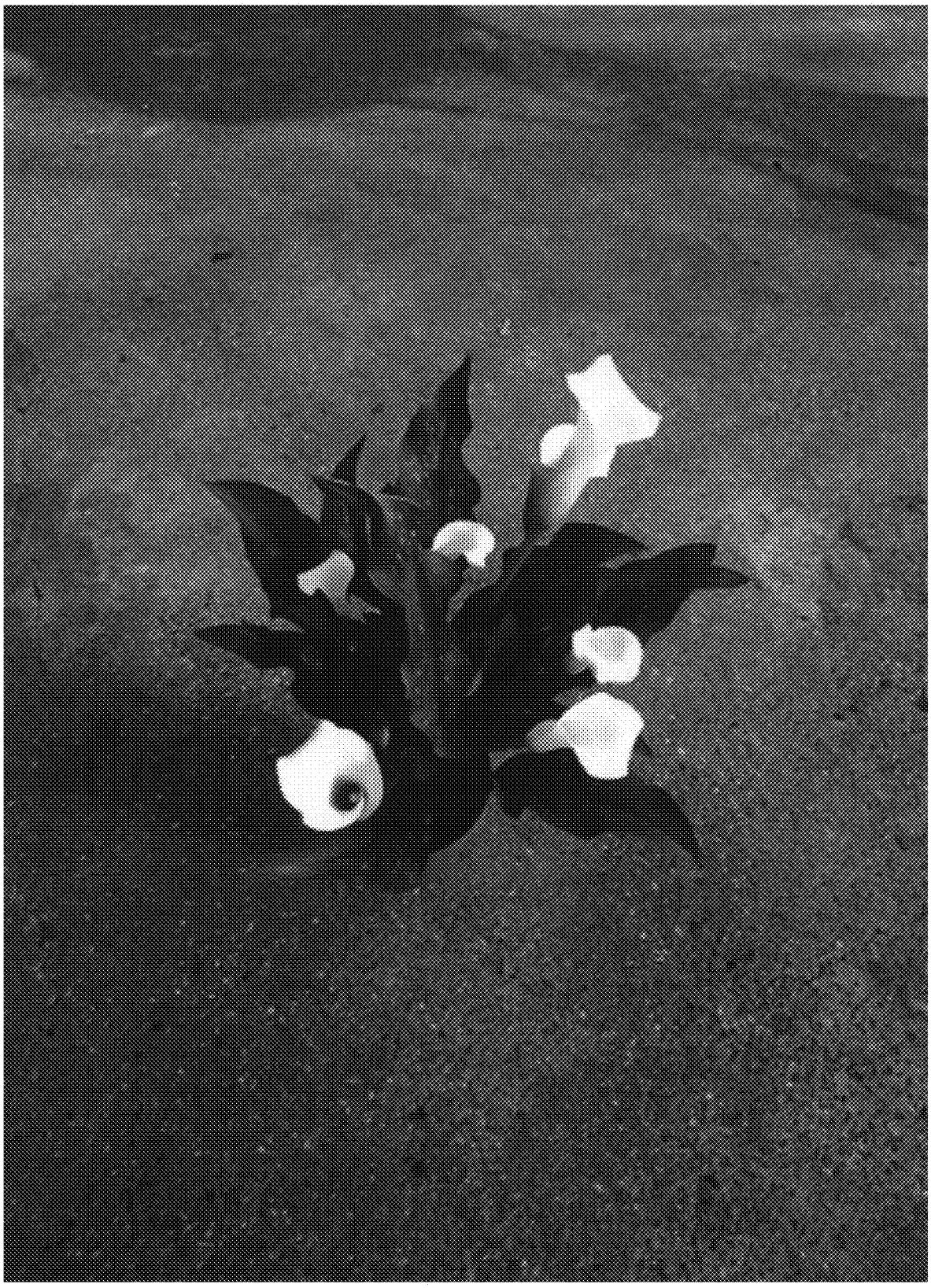
FIG. 1 illustrates a single flowering plant of the new variety.
Figure 2:
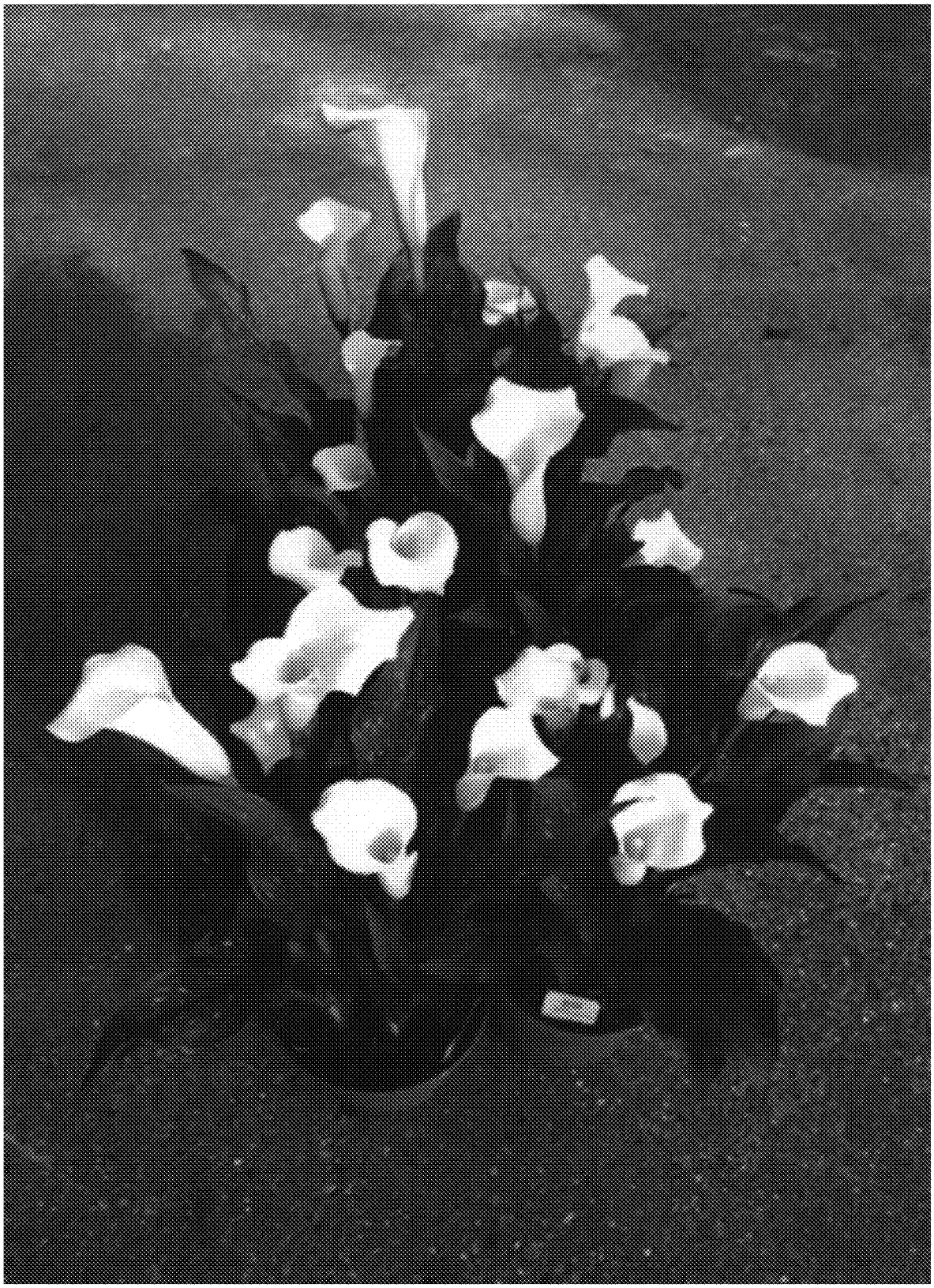
FIG. 2 illustrates multiple flowering plants of the new variety.

Type: Deciduous.

Size:

*Height of the leaf canopy above the soil.*—15-21 cm.

*Height of top of inflorescences above the soil.*—30-40 cm.

*Diameter.*—30-36 cm.

Form: Semi-spreading.

Number of inflorescences per tuber:

*Size* 16-18 *cm in diameter.*—6-10 inflorescences.

Branches:

*Number.*—Average.

*Color.*—Yellow-Green Group RHS 144C.

*Young shoot color.*—Yellow-Green Group RHS 145A to 145B.

Leaves:

*Size.*—Width: 5-8.5 cm, with the broadest part being slightly below the middle. Length: 17-23 cm.

*Number per plant.*—22-28.

*Leaf blade lobes.*—Absent.

*Shape.*—Lanceolate.

*Apex.*—Apiculate.

*Base.*—Attenuate.

*Margin.*—Entire; having a color of Yellow-Green Group RHS 147B to 147C.

*Color.*—Upper surface: Yellow-Green Group RHS 147A to 147B, with medium, linear White Group RHS 155A to 155B maculations present. Lower surface: Yellow-Green Group RHS 146B to 146C, with medium, linear White Group RHS 155C to 155D maculations present.

*Veins.*—Configuration: Pinnate. Color: Yellow-Green Group RHS 144B to 144C.

*Surface texture.*—Smooth (both surfaces).

*Petiole.*—Length: 13-22 cm. Diameter: 10-13 mm. Color: The base is Greyed-Orange Group RHS 165B to 165C, the upper part is Yellow-Green Group RHS 146B to 146C.

Roots:

*Color.*—White Group RHS 155C.

*Branching description.*—Fibrous root system. Several main roots emerge from the top of the tuber and form a small number of lateral roots.

Spathe:

*Size.*—Length (measured from opening to tip): 4.5-6.5 cm. Width: 4.5-6 cm. Height: 6.5-8 cm.

*Color.*—Throat spot: Greyed-Purple Group RHS 186C. Upper surface: White Group RHS 155A to 155B. Lower surface: Yellow-Green Group RHS 145C to 145D.

*Vein color.*—Green-White Group RHS 157C to 157D.

*Shape.*—Cupped.

*Apex.*—Apiculate.

*Base.*—Amplexicaul.

*Margin.*—Entire, with a color of Yellow-Green Group RHS 145D.

Spadix:

*Shape.*—Cylinder.

*Size.*—Length: 35-45 mm. Diameter: 9-11 mm.

*Color.*—Yellow-Orange Group RHS 15A to 15B.

*Position relative to spathe.*—Upright.

Peduncle:

*Size.*—Length: 23.5-34 cm. Diameter: 10-13 mm.

*Color.*—The upper part is Yellow-Green Group RHS 145A to 145B, the lower part is Greyed-Orange Group RHS 174C to 174D.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: Between 480 and 600. Pollen amount: Scarce. Color: Between White Group RHS 155B and 155C.

*Anther.*—Shape: Round. Length: Less than 1 mm. Color: Yellow Group RHS 8B to 8C.

*Filament.*—Length: Less than 1 mm. Color: White Group RHS 155D.

*Pistils.*—Number: 15 to 30. Length beyond perianth: About 1 mm.

*Stigma.*—Shape: Round. Size: Less than 1 mm.

*Style.*—Length: Less than 1 mm. Color: Yellow Group RHS 8B to 8C.

*Ovaries.*—Texture: Smooth. Length: Between 1 to 10 mm. Width: Between 1 to 10 mm. Color: The top color is Yellow-Orange Group RHS 16A to 16B, the bottom color is Yellow Group RHS 3A to 3B.

Seeds:

*Length.*—2.3-3.8 mm.

*Width.*—1.8-3.7 mm.

*Color.*—Greyed-Green Group RHS 197B to 197C.

*Amount.*—8 per inflorescence.

Disease resistance: No unusual susceptibility/resistance to diseases noticed to date.

Pest resistance: No unusual susceptibility/resistance to pests noticed to date.

Heat tolerance: No heat tolerance.

Hardiness: Not tested to date.

Flowering: In general, the time from indoor and outdoor planting to first flowering takes about eight weeks in The Netherlands.

Lastingness: About two weeks on the plant.

Fragrance: None.

I claim:

1. A new and distinct variety of calla lily plant named 'Dozanwhiho' as herein described and illustrated.

* * * * *